United States Patent [19]

Ryan

[11] Plant 4,448

[45] Aug. 14, 1979

[54] IMPATIENS PLANT

[76] Inventor: John J. Ryan, 39877 Sundale Dr., Fremont, Calif. 94538

[21] Appl. No.: 875,597

[22] Filed: Feb. 6, 1978

[51] Int. Cl.[2] ..... A01H 5/00
[52] U.S. Cl. ..... Plt./68
[58] Field of Search ..... Plt./68

[56] References Cited

U.S. PATENT DOCUMENTS

P.P. 2,206 12/1962 Rubel ..... Plt./60

*Primary Examiner*—Robert E. Bagwill
*Assistant Examiner*—James R. Feyrer
*Attorney, Agent, or Firm*—James R. Cypher

[57] ABSTRACT

This invention relates to a new and distinct variety of New Guinea Impatiens plant known by the cultivar name Shoshoni, and discovered by me in commercial greenhouses in Fremont, Calif. Shoshoni is closest in characteristics to Red Magic, but is particularly characterized by its orange flowers; color breaks to a very light orange; a less succulent growth; and very floriferous as is Red Magic with a similar dark foliage.

3 Drawing Figures

BACKGROUND OF THE INVENTION

The present new variety (seedling) was discovered by me in a commercial greenhouse in Fremont, Calif. as a result of the cross pollination of the pistil parent 76-13-1 (Maya) U.S. Plant Pat. No. 4,258, granted June 6, 1978 and the unpatented pollen parent 76-58-2.

Asexual reproduction of my new cultivar by terminal or stem cuttings grown in pots in a plastic (polyethylene) greenhouse in Fremont, Calif., under normal environmental conditions show that the characteristics described come true to form and are established and transmitted through succeeding propagations.

Color readings were taken during daylight hours in full sun, and all colors are based on the Royal Horticultural Society Colour Chart.

BRIEF SUMMARY

Shoshoni is closest in characteristics to Red Magic. The following outstanding characteristics of Shoshoni distinguish it from Red Magic:

1. Floriferousness equals or surpasses Red Magic.
2. Flower color is orange with very light orange color breaks. Two color breaks occur; a darker one 40D, seen only occasionally, and a lighter one 49D which is the common color break that occurs approximately 2% of the time, i.e. approximately 2% of the blossoms will show the lighter color break.
3. Shoshoni is less succulent.
4. Foliage is not as large or as dark as RED MAGIC.

DESCRIPTION OF THE PHOTOGRAPH

The accompanying colored photograph of the entire plant illustrates the overall appearance of the cultivar Shoshoni, showing the colors as true as reasonably possible for this type of colored reproduction. Under high light the foliage darkens and the flower lightens a little. Supplemental photographs B and C show the lighter color break that is the commonly occurring color break. Photographs B and C (photograph B is a close up of photograph C) depict two typical blossoms that show the orange flecked color break as it normally occurs, and a third blossom whose petals are composed of approximately 40% of the orange flecked color break, which only occurs rarely, but is a good illustration of the color of the breaks. Background color of the flecks is light orange fading into white.

DETAILED DESCRIPTION

The following detailed description of Shoshoni was based on observations made of the new cultivar on Nov. 4, 1977.

I. PLANT

Name: Shoshoni.
Origin: Seedling of the cross pollination of the pistil parent 76-13-1 (Maya) U.S. Pat. application, Ser. No. 782,284 filed 3-28-77 and the unpatented pollen parent 76-58-2.
Form: Upright to spreading.
Height to flowering: 30 cm. to 38 cm.
Growth: Moderate.
Type of cutting: Terminal or stem.
Rooting time: Typical, 10–14 days.
Rooting habit: Fast dendritic.

II. FOLIAGE

Arrangement: Lower leaves on any break opposite (usually just one set); upper foliage of any break, whorls of 3 to 5.
Shape: Older leaves of any break usually oblanceolate; upper leaves are elliptical.
Tip: Acuminate.
Base: Attenuate.
Margin: Serrulate.
Veination: Pinnate.
Size: Blade and petiole 7.0 cm. to 11.5 cm.; length of blade 5.5 cm. to 9.0 cm.; width at widest point 1.5 cm. to 3.5 cm.
Surface:
1. *Smoothness.*—Occasionally crinkled.
2. *Texture.*—Glabrous, semi-glossy.

Variegation: None.
Color:
1. *Petioles.*—Upper surface 185 B, lower surface 185 A.
2. *Veins.*—Lower surface 185 A, upper surface 185 B to 185 D.
3. *Leaf.*—a. Upper 139 A. b. Lower 183 A to 183 B.

III. STEM

Color: 185 A to 185 B.
Internode:
1. *Length.*—Moderate.
2. *Size.*—Moderate.

Node expanded (relative to internode): Slightly expanded.
Breaking action: Average.

IV. FLOWER

Form: Typical.
Borne: End of branches, terminal.
Blooming habit:
1. *Relative number.*—Very good to profuse.
2. *Time to flowering.*—Short to average.
3. *Longevity.*—Typical, 3 to 5 days.

Size of mature flower: First flower on a plant may be small.
1. *Length.*—5.0 cm. to 5.5 cm.
2. *Width.*—4.5 cm. to 5.0 cm.
3. *Spur.*—5.5 cm. to 6.0 cm.

Color:

| | |
|---|---|
| 1. *Eye:* 58 B. | |
| 2. *Middle* | 33 A. |
| 3. *Edge* | |
| 4. *Pedicel:* 145 C to 145 D. | |

V. REPRODUCTIVE ORGANS

Stamen:

| | |
|---|---|
| 1. *Anthers* | Typical, fused hood over pistil. |
| 2. *Filaments* | |
| 3. *Pollen.* a. Color: 8 D. b. Abundance: Varies greatly, but viability poor. | |

Pistils:

| | |
|---|---|
| 1. *Style* | Typical. |
| 2. *Ovaries* | |

VI. OTHER CHARACTERISTICS

Disease: Shoshoni is more resistant than other varieties to most soft rots.

I claim:

1. A new and distinct form of Impatiens plant, as described and illustrated, known by the cultivar name Shoshoni, and particularly characterized by its orange flower; color breaks to a very light orange; a less succulent growth than Red Magic; and very floriferous as is Red Magic with a similar dark foliage.

* * * * *

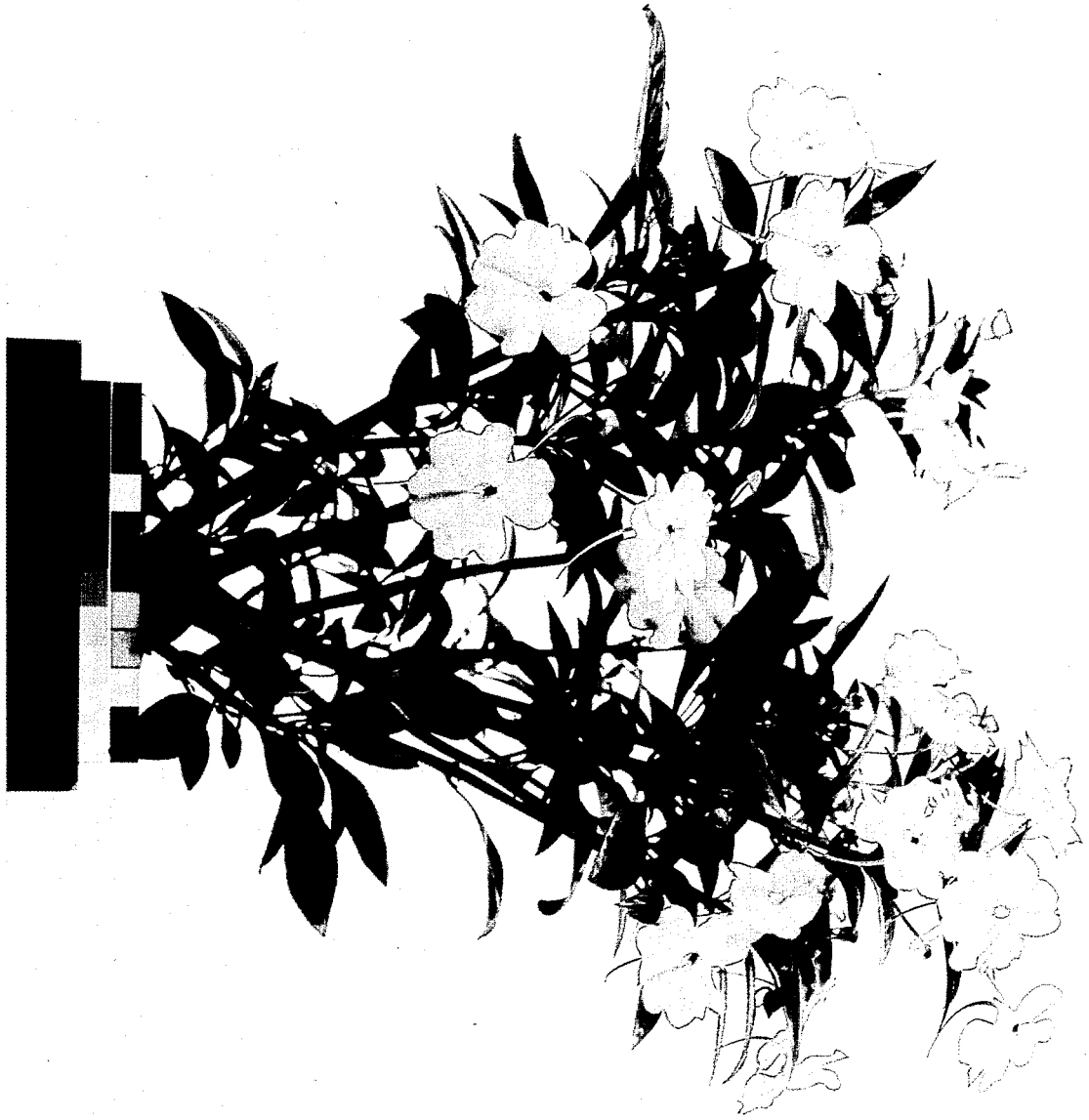

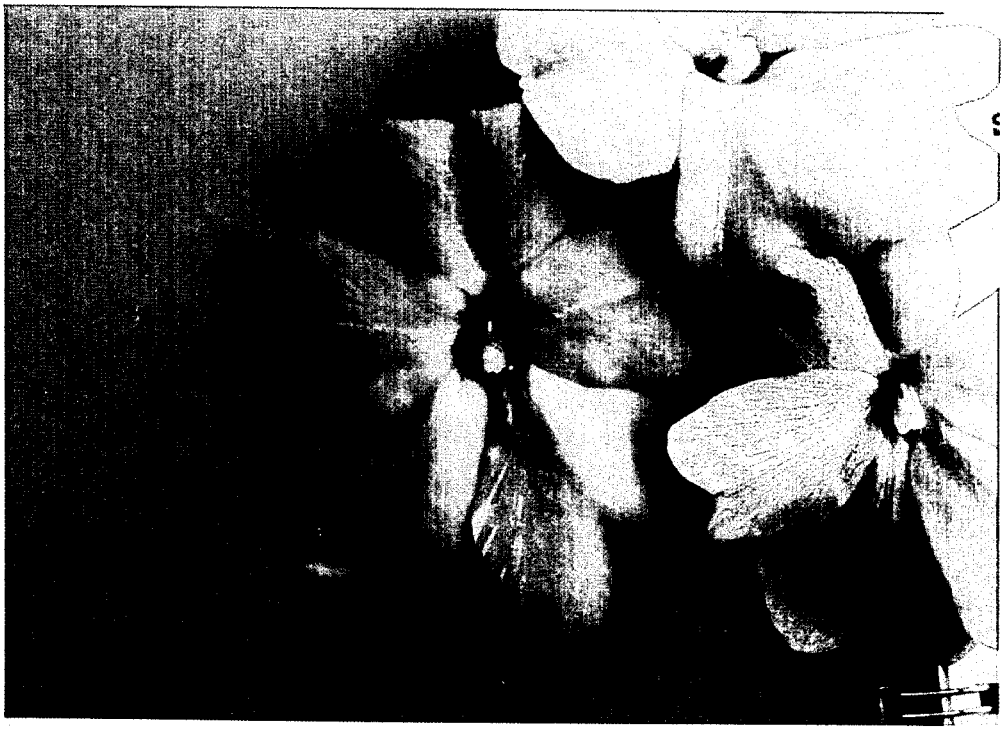

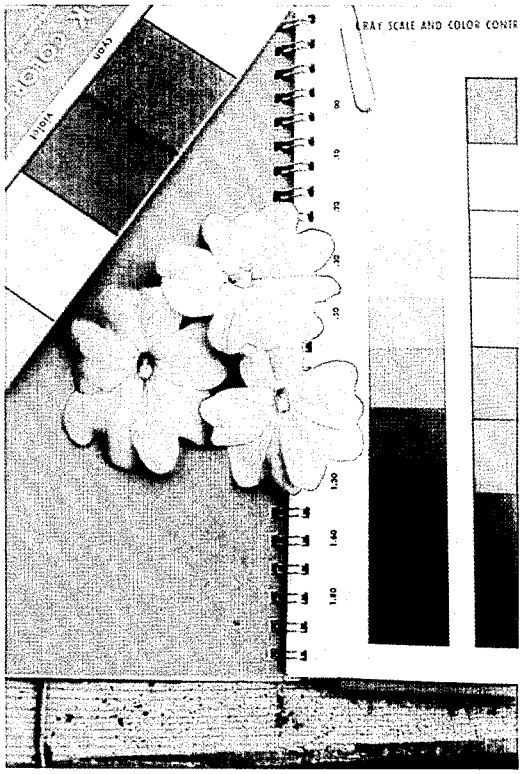
INDIA
USA
GRAY SCALE AND COLOR CONTR